United States Patent [19]

Wellershaus

[11] Patent Number: 4,574,790

[45] Date of Patent: Mar. 11, 1986

[54] ORTHOPEDIC DEVICE FOR TREATING HIP DYSPLASIA AND HIP DISLOCATION

[75] Inventor: Ulf Wellershaus, Duderstadt, Fed. Rep. of Germany

[73] Assignee: Otto Bock Orthopädische Industrie KG, Duderstadt, Fed. Rep. of Germany

[21] Appl. No.: 550,594

[22] Filed: Nov. 9, 1983

[30] Foreign Application Priority Data

Jul. 9, 1983 [DE] Fed. Rep. of Germany ... 8319895[U]

[51] Int. Cl.$^4$ ............................................. A61F 5/02
[52] U.S. Cl. ................................. 128/78; 128/80 A; 128/87 C
[58] Field of Search ................... 128/78, 80 A, 80 C, 128/80 F, 83, 84 B, 87 C, 92 R, 92 A

[56] References Cited

U.S. PATENT DOCUMENTS 3,759,252 9/1973 Berman ..................... 128/80 A X
4,497,315 2/1985 Fettweis et al. .................. 128/78

FOREIGN PATENT DOCUMENTS 3030712 3/1982 Fed. Rep. of Germany .... 128/87 C
3113981 11/1982 Fed. Rep. of Germany .
0827061 5/1981 U.S.S.R. ........................... 128/92 A Primary Examiner—Richard J. Apley
Assistant Examiner—Alan W. Cannon
Attorney, Agent, or Firm—Michael J. Striker

[57] ABSTRACT

In an orthopedic device for treating hip dysplasia and hip dislocation, a pelvis-supporting portion is provided with two angular projections extending in the region of natural hip joints of a patient and each carrying a pivot joint including rotation discs to which a curved guide is connected. The curved guide of each pivot joint has a longitudinal slot in which an end of an upper shank guide bar is displaceable and arrestable in any desired position. Two upper shank guide bars carrying the respective upper shank supports are pivotally connected to the lower shank guide bars carrying the respective lower shank supports.

4 Claims, 4 Drawing Figures

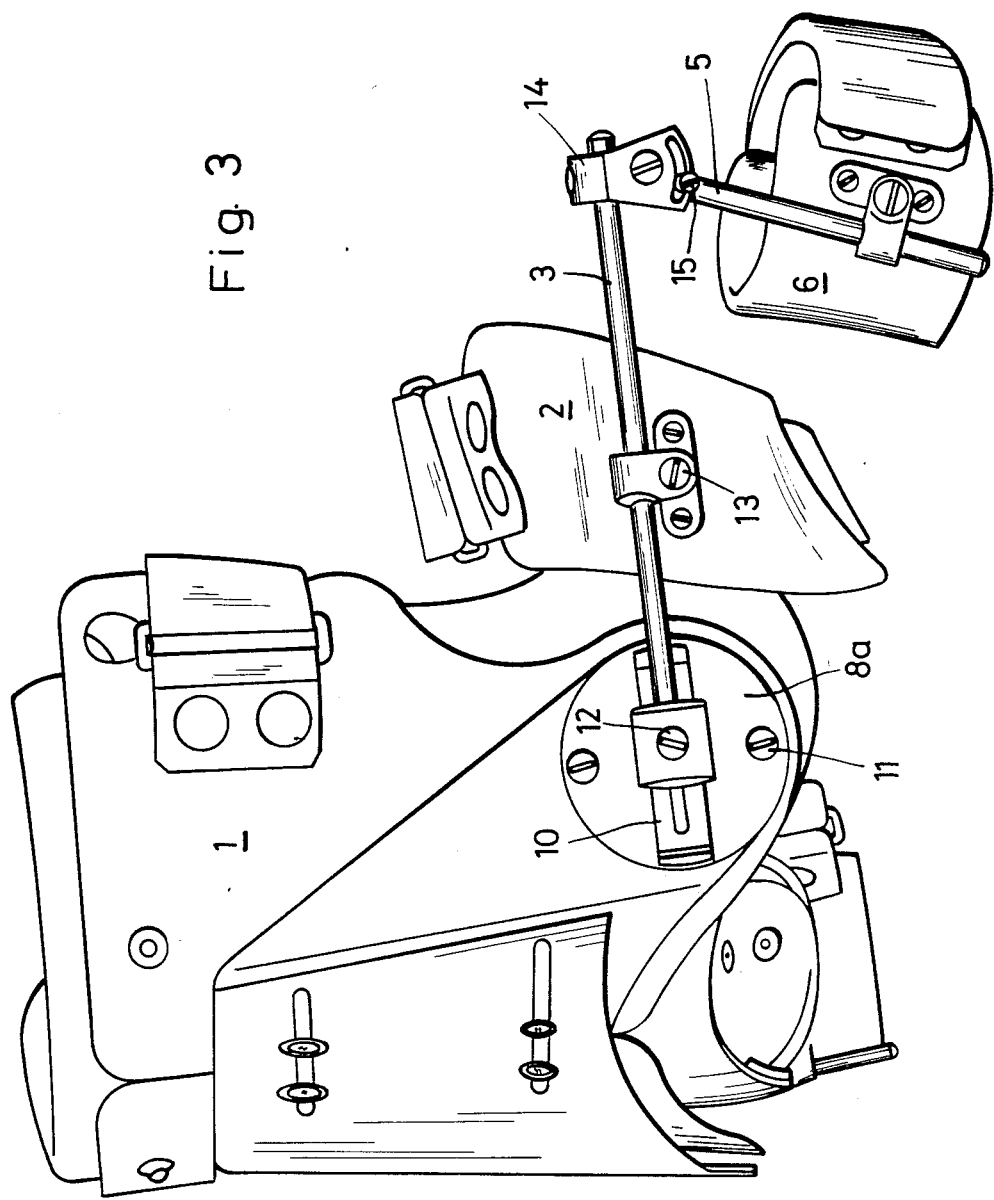

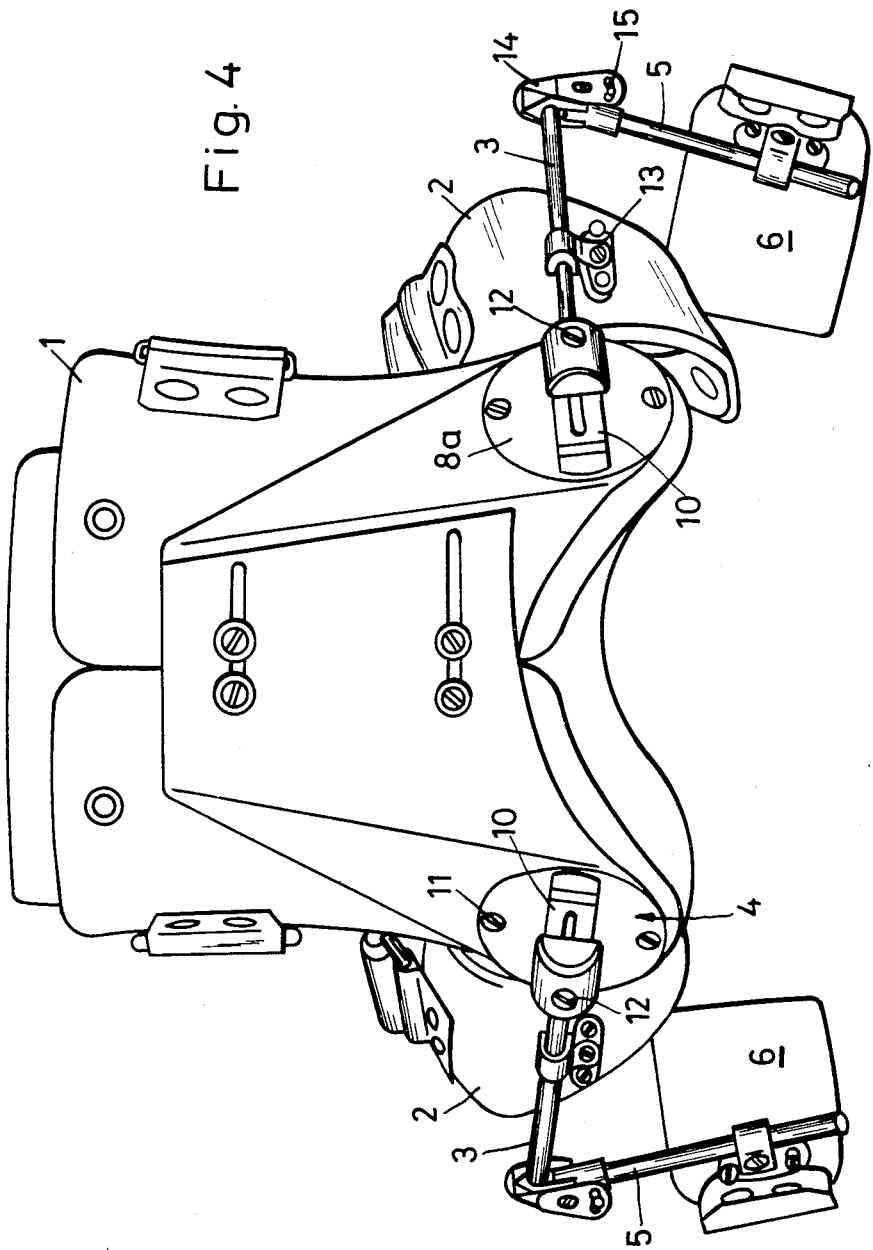

ORTHOPEDIC DEVICE FOR TREATING HIP DYSPLASIA AND HIP DISLOCATION

BACKGROUND OF THE INVENTION

The present invention relates to orthopedic devices for treating hip dysplasia and hip dislocation.

Normally the treatment of patients having hip dysplasia or hip dislocation has been carried out in two phases. The first phase includes a reposition of a hip joint head in a seat. The second phase must be a retention or securing of the aligned hip joint head in the most favorable position.

Orthopedic device for treating hip dysplasia and hip dislocation of the type under consideration have been known in the art. One of such devices is disclosed in the German Pat. No. DE 31 13 981 C1. The known device comprises a pelvis-supporting portion and two upper shank supports held on upper shank guide bars. The ends of the upper shank guide bars are, in the regions of natural hip joints, pivotally connected to the pelvis-supporting portion. The pivoting movement is effected by a pivot mounted between the upper shank bar and the pelvis-supporting portion and formed of a ball-and-socket joint, the movable pivot part of which is arrestable in any angular position. Another pivotable member is arranged between the movable pivot part and the upper shank guide bar. The upper shank guide bar is pivotable about the pivot axis of this pivotable member independently from the position of the ball pivot and can be locked or arrested in any desired position. The movable socket portion, which receives the ball pivot, includes a rotation-symmetrical sleeve or bush which has a sloped surface which is connected to the pelvis-supporting portion so that the axes of the bushes of both joints include with each other an angle of approximately 90°.

The utilization and the mode of operation of the known orthopedic device are described in the aforementioned patent.

Each of the two joints in the conventional orthopedic device lies in the region of the natural hip joint; therefore the device is defined by the height of the ball sockets, by the location of the components of the device outside the pelvis-supporting portion and depending on how far extends the above mentioned rotation-symmetrical bush from the natural hip joint. All the above limitations have caused certain adjustment difficulties of the orthopedic device; for example, before releasing the upper shank supports it has been necessary, during the pivoting of the upper shank guide bar, to cause by the above pivoting a necessary displacement of the upper shank of a patient with respect to the upper shank support.

SUMMARY OF THE INVENTION

It is an object of the present invention to provide an improved orthopedic device for treating hip dysplasia and hip dislocation.

It is another object of the invention to provide an orthopedic device which is easy to handle.

These and other objects of the invention are attained by an orthopedic device for treating hip dysplasia and hip dislocation, comprising a pelvis-supporting portion; two upper shank guide bars laterally extended from said pelvis-supporting portion and carrying two upper shank supports, respectively, said upper shank guide bars having ends pivotally connected to said pelvis-supporting portion in the regions of natural hip joints of a patient by joint means and being adjustable with respect to the pelvis-supporting portion in any desired angular position; and two lower shank guide bars connected respectively to said upper shank guide bars and carrying two respective lower shank supports, the pelvis-supporting portion including two angularly extending projections extending in the regions of the natural hip joints, said joint means each including rotative means abutting against the respective projection, said rotative means being rotatable about an axis extended perpendicularly to said respective projection and being arrestable in any desired rotation position, and a curved guide connected to said rotative means and spaced therefrom at a distance which varies over the length of the guide, the end of the respective upper shank guide bar being displaceably guided in said curved guide and adapted to be arrested in any desired position with respect thereto.

The curved guide may be formed with a guide slot in which the end of the respective upper shank guide bar is displaceable.

Each of the upper shank supports may be pivotable about a longitudinal axis of the respective upper shank guide bar and arrestable thereon in any desired position.

The substantial distinction between the orthopedic device suggested herein and the conventional devices of this type resides in that the rotation of the upper shank guide bar in the present invention takes place immediately within the plane of the respective projection of the pelvis-supporting portion near the anatomic hip joint centre and not at the distance therefrom. The rotation of the artificial joint is better adjusted to the rotation of the natural hip joint. This possibility of rotation has, in connection with the adjustment of the upper shank guide bar in respect to the curved guide, a lower degree of freedom as compared to the construction having the ball-and-socket joint; this freedom can now be realized without a specific joint, merely by pivoting the upper shank support about the longitudinal axis of the respective upper shank guide bar. It is also possible that the upper shank support could be pivoted together with the respective guide bar about the axis of elongation of the bar. It is also expedient that the upper shank support should be pivotally positioned on the upper shank guide bar so that a relative pivoting movement would be possible between these two components.

The above mentioned rotative means may include two circular discs spaced from each other to receive the respective projection of the pelvis-supporting portion therebetween and clamping screws for arresting the discs to each other in and desired rotation position.

According to a further concept of the invention the axes of both rotative means may include with each other an angle $\beta$ of about 90°.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawing.

BRIEF DESCRIPTION OF THE DRAWINGS

FIG. 3 is a perspective side view of the orthopedic device; and

FIG. 4 is a perspective rear view of the device shown in FIG. 1.

DETAILED DESCRIPTION OF THE PREFERRED EMBODIMENT

Figure 1:
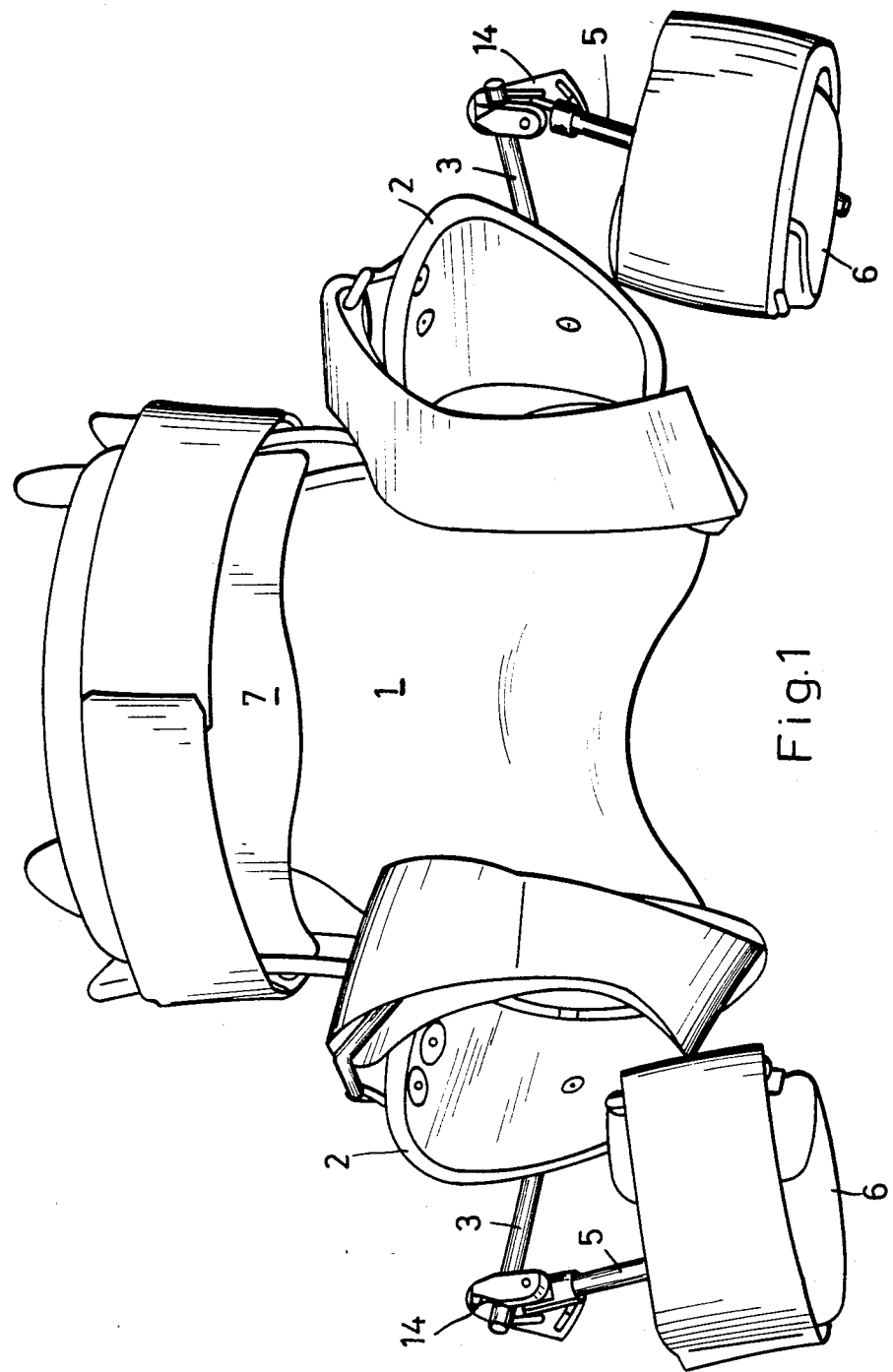
FIG. 1 is a perspective front view of the orthopedic device according to the invention.

Referring now to the drawings, an orthopedic device for treating a hip dysplasia and hip dislocation comprises a pelvis-supporting portion 1 and two upper shank supports 2 which are respectively connected to two lateral upper shank guide bars 3. The ends of guide bars 3 are pivotally mounted to the pelvis or basin-supporting portion 1 in the regions of two natural hip joints. The pivoting is effected by means of pivot joints 4. The ends of the guide bars may be pivoted about joints 4 and adjusted in any desired angular position.

Each upper shank guide bar 3 is, at its end opposite to the respective joint 4, releasably and pivotally connected to a lower shank guide bar 5 via a connecting member 14. Each guide bar 5 is in turn connected to a respective lower shank support 6. The basin portion as well as the upper shank supports 2 and lower shank supports 6 have each a half-shell configuration. The pelvis-supporting portion 1 is fitted to an abdomen plate 7 and hingedly mounted thereto.

Each pivot joint 4 includes a rotation portion which flatly lies on a respective flat laterally-extended projection 1a formed on the rear side of the pelvis portion (FIG. 2) of the orthopedic device. This rotation portion of the joint 4 is formed of two circular discs 8a and 8b spaced from each other to receive therebetween the above mentioned projection 1a. It is, of course, understood that the right-hand and the left-hand joints 4 corresponding to the right and left legs of a patient, are constructed identically to each other. The circular discs 8a and 8b of the rotation portion of each joint with the respective projection 1a included therebetween are clamped to each other by means of two clamping screws 11. Both circular discs 8a, 8b can be mutually rotated one with respect to the other about a rotation axis 9 which extends perpendicularly to the respective projection 1a of the pelvis-supporting portion. Each axis 9 can be formed by a pin or a screw extending through the center of the respective disc. Upon tightening of both clamping screws 11 the circular discs 8a, 8b are rigidly clamped to the projection 1a of the pelvis-supporting portion 1 and are therefore adjusted in a desired position.

Figure 2:
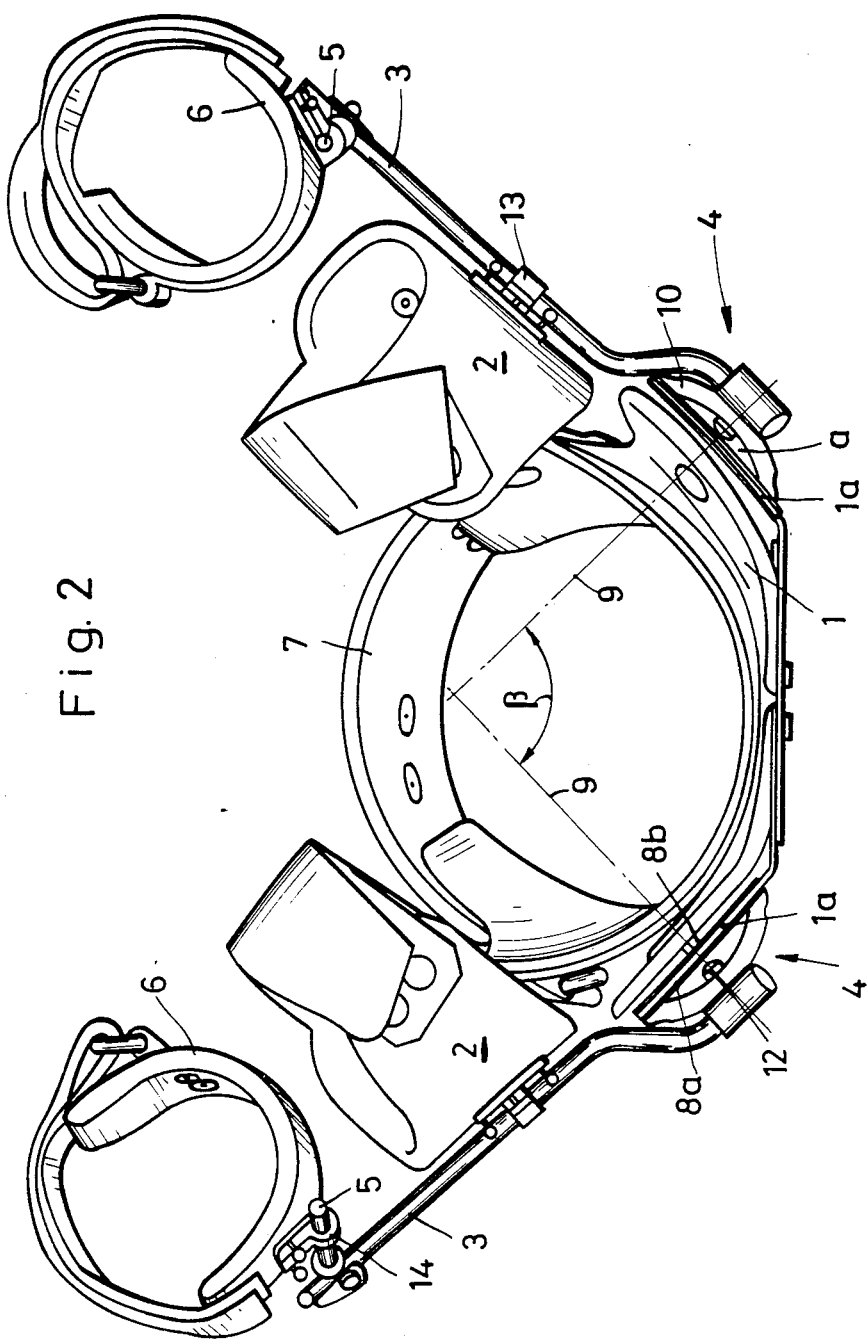
FIG. 2 is a perspective view of FIG. 1 seen from below.

As shown in FIGS. 2 and 4, a curved guide 10 is provided at each joint 4. The curved guide 10 is connected to the disc 8a lying against the outer side of the projection 1a of the pelvis portion. This curved guide is spaced from the disc 8a over the entire length of the guide 10 at a variable distance designated by reference "a" as seen in FIG. 2. This curved guide 10 is guided in a bridge-like fashion over the middle diameter of disc 8a. A guide slot 10' is formed in the guide 10, in which a clamping member 12 secured to the end of the upper shank guide bar 3 is displaceable, whereby the latter can be adjustably guided in slot 10' and fixed to the guide 10 in any desired position.

The upper shank support 2 is pivotably supported on the respective upper shank bar 3 and is able to be adjusted in a desired pivotable position with respect to the upper shank bar by means of tightening of a clamping device 13.

FIG. 2 illustrates that an angle β included between two rotation axes 9 of both pivot joints 4 is about 90°.

The lower shank guide bars 5 are displaceable on the respective upper shank guide bars 3 by means of tubular clamping elements 14 and can be secured at any desired position on the bars 3 by any suitable conventional means. In addition, each lower shank guide bar 5 carrying the lower shank support 6 is pivotable in respect to the clamping element 14 on a pivot connected to the clamping element 14 and is adjustable in any desired pivotable position by tightening of a clamping screw inserted into a curved slot 14' formed in the respective clamping element 14.

Connecting devices 13, 13' for connecting the upper shank and lower shank supports to the respective guide bars are further provided in the orthopedic device. Due to sleeve 13a the upper shank support 2 is pivotable about the longitudinal axis of bar 3. Support 2 can be also adjusted on bar 3 in any desired angular position by tightening respective screws.

It will be understood that each of the elements described above, or two or more together, may also find a useful application in other types of orthopedic devices differing from the types described above.

While the invention has been illustrated and described as embodied in an orthopedic device, it is not intended to be limited to the details shown, since various modifications and structural changes may be made without departing in any way from the spirit of the present invention.

Without further analysis, the foregoing will so fully reveal the gist of the present invention that others can by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. An orthopedic device for treating hip dysplasia and hip dislocation, comprising a pelvis-supporting portion; two upper shank guide bars laterally extended from said pelvis-supporting portion and carrying upper shank supports, respectively, said upper shank guide bars having ends pivotally connected to said pelvis-supporting portion in the regions of natural hip joints of a patient and being adjustable with respect to said pelvis-supporting portion in any desired angular position; each of said upper shank supports being pivotable about the longitudinal axis of the respective upper shank guide bar and arrestable thereon in any desired position; joint means for connecting said ends to said pelvis-supporting portion; and two lower shank guide bars connected respectively to said upper shank guide bars and carrying two respective lower shank supports, the pelvis-supporting portion including two angularly extending projections extending in the regions of natural hip joints, said joint means each including rotative means being rotatable only about an axis extended perpendicularly to said respective projection and being arrestable in any desired rotation position, and a curved guide connected to said rotative means and spaced therefrom at a distance which varies over the length of the guide, the end of the respective upper shank guide bar being displaceably guided in said curved guide and adpated to be arrested in any desired position with respect thereto.

2. The device as defined in claim 1, wherein said curved guide is formed with a guide slot in which the end of the respective upper shank guide bar is displaceable.

3. The device as defined in claim 1, wherein said rotative means include two circular discs spaced from each other to receive the respective projection of the pelvis-supporting portion therebetween and clamping screws for arresting the discs to each other in any desired rotation position.

4. The device as defined in claim 3, wherein the axes of both rotative means include with each other an angle $\beta$ of about 90°.

* * * * *